United States Patent
Liu et al.

(10) Patent No.: US 12,297,228 B2
(45) Date of Patent: May 13, 2025

(54) METHOD FOR EXTRACTING USEFUL SUBSTANCES FROM SHRIMP SHELLS

(71) Applicant: HUNAN BEIBEISHENG BIOTECHNOLOGY INDUSTRIAL CO., LTD., Changsha (CN)

(72) Inventors: Yusen Liu, Changsha (CN); Hongchang Liu, Changsha (CN)

(73) Assignee: HUNAN BEIBEISHENG BIOTECHNOLOGY INDUSTRIAL CO., LTD.

( * ) Notice: Subject to any disclaimer, the term of this patent is extended or adjusted under 35 U.S.C. 154(b) by 784 days.

(21) Appl. No.: 17/610,129

(22) PCT Filed: May 13, 2020

(86) PCT No.: PCT/CN2020/089910
§ 371 (c)(1),
(2) Date: Nov. 9, 2021

(87) PCT Pub. No.: WO2020/228713
PCT Pub. Date: Nov. 19, 2020

(65) Prior Publication Data
US 2022/0135616 A1  May 5, 2022

(30) Foreign Application Priority Data
May 14, 2019  (CN) .......................... 201910397107.7

(51) Int. Cl.
| | |
|---|---|
| C07K 1/14 | (2006.01) |
| B01D 17/02 | (2006.01) |
| B01D 21/26 | (2006.01) |
| B01D 33/03 | (2006.01) |
| C07C 403/24 | (2006.01) |
| C07K 1/34 | (2006.01) |
| C07K 1/36 | (2006.01) |
| C07K 14/435 | (2006.01) |
| C08B 37/00 | (2006.01) |
| C08B 37/08 | (2006.01) |
| C12P 7/26 | (2006.01) |

(52) U.S. Cl.
CPC .......... *C07K 1/145* (2013.01); *B01D 17/0217* (2013.01); *B01D 21/262* (2013.01); *B01D 33/03* (2013.01); *C07C 403/24* (2013.01); *C07K 1/34* (2013.01); *C07K 1/36* (2013.01); *C07K 14/43509* (2013.01); *C08B 37/0003* (2013.01); *C08B 37/003* (2013.01); *C12P 7/26* (2013.01)

(58) Field of Classification Search
None
See application file for complete search history.

(56) References Cited

FOREIGN PATENT DOCUMENTS

| | | |
|---|---|---|
| CN | 1775816 A | 5/2006 |
| CN | 103172763 A | 6/2013 |
| CN | 109735392 A | 5/2019 |
| CN | 110143903 A | 8/2019 |
| WO | 2020228713 A1 | 11/2020 |

OTHER PUBLICATIONS

Fransen,. CHJM; The Living Marine Resources of the Eastern Central Atlantic, vol. 1; Chapter: Shrimps and Pawns; pp. 37-196, 2014 (Year: 2014).*
International Search Report for related International Application No. PCT/CN2020/089910, dated Aug. 6, 2020, 5 pages.
Song, "Extraction and Puirifcation of Astaxanthin from Antarctic Krill Shells", Chinese Master's Theses Full-Text Database, Engineering Science and Technology 1, 2013, Translation of pp. 3 and 10.

* cited by examiner

*Primary Examiner* — David W Berke-Schlessel
(74) *Attorney, Agent, or Firm* — DITTHAVONG, STEINER & MLOTKOWSKI

(57) ABSTRACT

Disclosed is a method for extracting useful substances from shrimp shells. The method comprises: crushing the shrimp shells, mixing the crushed shrimp shells and water, then heating same to 28° C.-35° C., adjusting the pH value to 6.8-7.5, preferably 6.8-7, then adding an alkaline protease and mixing same, heating same to 42° C.-48° C., performing constant-temperature enzymolysis for 50-70 min, and performing sieving to obtain an enzymatic hydrolysate and solid residues; performing centrifugal separation treatment on the enzymatic hydrolysate to obtain a shrimp protein deposit containing astaxanthin; mixing the shrimp protein deposit and water, performing heating while stirring, adjusting the pH value to 6.8-7.0, performing heating to 58° C.-60° C., adding vegetable oil, and performing emulsification for 50-70 min under stirring to obtain an emulsion; and performing centrifugation on the emulsion, and performing delamination to obtain astaxanthin-containing oil in an upper layer, water in a middle layer, and a shrimp protein in a lower layer. The method of the present invention uses waste biomass obtained after shrimps processed as a raw material, and can simultaneously extract several high-value substances, thereby not only improving the utilization rate of the raw material, but also shortening the production cycle; and no organic solvent is added, such that the method is clean, green and environmentally friendly.

19 Claims, No Drawings

METHOD FOR EXTRACTING USEFUL SUBSTANCES FROM SHRIMP SHELLS

FIELD OF THE INVENTION

The present invention relates to a method for extracting useful substances from shrimp shells, in particular to a method for extracting useful substances such as astaxanthin, shrimp protein chitosan, and calcium citrate from shrimp shells by a biological enzyme method.

BACKGROUND OF THE INVENTION

The chemical name of astaxanthin is 3,3'-dihydroxy-4,4'-diketo-β,β'-carotene, pigment Aj067-69, CASNO: 472-62-7, and its molecular formula is $C_{40}H_{52}O_4$, its molecular weight is 596.86. Pure astaxanthin is reddishdark brown with a melting point of 224° C., insoluble in water, and soluble in most organic solvents. It is a red pigment that can give ornamental fish, salmon, shrimp and flamingo pink color. Astaxanthin has super anti-oxidant ability, and also has the functions of resisting tumors, resisting senility, strengthening body immunity, and preventing cardiovascular and cerebrovascular diseases. Therefore, astaxanthin is widely used in industries such as functional food, medicine, cosmetics, and poultry and aquatic feed, with huge market potentials. Although there are currently many methods for extracting astaxanthin, they still have some technical deficiencies. Natural astaxanthin often exists in some animals, algae and microorganisms, and its production may include extraction from animals and by-products thereof, or extraction from algae, and fermentation with microorganisms. At present, there are mainly five methods for extracting astaxanthin: alkaline extraction method, oil solution method, organic solvent method, supercritical $CO_2$ fluid extraction method, and biological enzyme method.

Alkaline extraction method: Alkaline extraction method mainly uses the principle of deproteinization with alkaline liquor. Most of the astaxanthin in carapace processing scraps is combined with protein and exists in the form of pigment-binding protein. When the scraps are boiled with hot alkaline liquor, the protein is dissolved out, and the astaxanthin bound to the protein is also dissolved out, so as to achieve the purpose of extracting astaxanthin. For example, the application No. CN02122565.6 discloses a method for producing chitin, astaxanthin and protein from fresh shrimp shells, in which a lot of acid and alkali are consumed during extraction, and it is difficult to eliminate the pollution of processing wastewater when shrimp shells are treated, which causes environmental pollution.

Oil solution method: Astaxanthin has good fat solubility, and the oil solution method is carried out just using this characteristic. However, in the oil solution method, due to difficult unsaturated fatty acids contained in various oils, their fat solution effects are also different. The extraction of astaxanthin may be affected by the acidity and alkalinity, saponification after exposure to water, etc., so it is best to use edible oil, such as soybean oil and safflower oil. In addition, it is difficult to concentrate pigment-containing oils after extraction and obtain high-concentration astaxanthin products, which limits the application range.

Organic solvent method: Organic solvent is an effective reagent for extracting astaxanthin. Usually, the solvent can be evaporated after extraction to concentrate the astaxanthin so as to obtain a relatively high concentration of astaxanthin oil. Meanwhile, the solvent is recycled. Common solvents include acetone, ethanol, ether, chloroform, n-hexane, etc. The organic solvent extraction method mainly uses extraction and reflux extraction methods, but the components of astaxanthin extracted by different extractants are quite different. The acetone, ethanol, and ether have safety and health problems during processing, and it is difficult to implement large-scale production.

Supercritical $CO_2$ extraction method: This technology is a high technology developed in recent years. The extracted products have attracted more and more attention because of their advantages of high purity, few solvent residues, no toxic side effects, etc. However, due to the large initial investment in equipment and high production technology requirements, this method is still difficult in large-scale industrial production at present.

Biological enzyme extraction method: For example, CN108559765A discloses a method for extracting N-acetyl-glucosamine and astaxanthin from crayfish shells by a biological enzyme method. This method requires test bacteria to culture a seed solution, and then the seed solution is transferred to a fermentation culture for fermentation to obtain a crude pure enzyme solution. During enzymolysis, after the enzyme solution is added, organic reagents should be added. This method is not full biological enzymolysis, and still uses organic reagents. The crude pure enzyme solution may play a catalytic role, and the procedures such as adsorbing with resin, eluting and washing with alcohol are also needed, so the process is complicated. In addition, the organic reagents used have safety and health problems.

SUMMARY OF THE INVENTION

In light of the shortcomings of the prior art, the objective of the present invention is to provide a method for extracting useful substances from shrimp shells, so as to extract useful substances such as astaxanthin and shrimp protein from shrimp shells through a process.

In order to solve the above technical problems, the technical solution of the present invention is as follows:

A method for extracting useful substances from shrimp shells, including the following steps:

S1, crushing the shrimp shells to obtain fragments;

S2, mixing the fragments obtained in S1 with water at a mass ratio of (1-2):(1-2) to obtain a mixture;

S3, heating the mixture obtained in S2 to 28-35° C. (preferably 30° C.), then adjusting the pH value to 6.8-7.5, preferably 6.8-7, adding an alkaline protease and mixing, heating to 42-48° C., performing constant-temperature enzymolysis, and sieving to obtain enzymatic hydrolysate and solid residues, wherein the mass ratio of the alkaline protease to the mixture is 1:(800-1200), preferably 1:1000, and continuous stirring at a rate of 45-60 revolutions per minute is required during the enzymolysis;

S4, performing centrifugal separation on the enzymatic hydrolysate obtained in S3 to obtain an astaxanthin-containing shrimp protein deposit;

S5, mixing the astaxanthin-containing shrimp protein deposit obtained in S4 with vegetable oil, heating to 57-60° C. while stirring, adding water, and emulsifying for 50-70 min, preferably 55-65 min under stirring to obtain an emulsion, wherein the mass ratio of the water to the shrimp protein deposit is (1.2-1.8):1, and the temperature difference between the mixture of shrimp protein deposit and vegetable oil and the added water is not more than 1° C.; and S6, centrifuging the emulsion in S5, and delaminating to obtain astaxanthin-containing oil in an upper layer, water in a middle layer, and a shrimp protein in a lower layer.

Optionally, the shrimp shells may be the shells of freshwater shrimp or sea shrimp, such as lobster and krill.

Further, in S1, the fragments have a size of 4-9 cm$^2$.

Further, in S3, the sieving is performed through an 80-mesh vibrating screen.

Further, in S3, the constant-temperature enzymolysis time is 50-90 min, further 50-70 min, preferably 60 min.

Optionally, the alkaline protease is a special compound enzyme preparation for animal proteins, optionally has an enzyme activity of 2 million U/g, and is mainly composed of endoproteinase, exonuclease and flavourease. The endonuclease severs a peptide chain inside a protein from the middle, the exonuclease severs the terminal of a polypeptide chain to release an amino acid, and the flavourease optimizes the bitterness and flavor of hydrolysis and is thus widely used in the hydrolysis of animal proteins.

Further, in S4, during the centrifugal separation, the centrifugal rate is 4000-5000 r/min, generally 4200-4800 r/min, and preferably 4500 r/min, and the centrifugal time is 10-14 min, preferably 12 min.

Further, in S5, the pH value is adjusted with glacial acetic acid or HCl.

Generally, the added amount of vegetable oil may be selected according to requirements. Optionally, in S5, the mass ratio of the vegetable oil to the shrimp protein deposit is (5-9):100. Further optionally, in S5, the mass ratio of the vegetable oil to the shrimp protein deposit is preferably 7:100.

Optionally, in S5, the mass ratio of the vegetable oil to the shrimp protein deposit is 7:(16.5-17.4). Optionally, in S5, 7 kg of vegetable oil is added to the astaxanthin-rich shrimp protein pulp corresponding to every 100 kg of enzymatic hydrolysate.

Optionally, in S5, the temperature difference between the mixture of shrimp protein deposit and vegetable oil and the added water is not more than 0.5° C.

Optionally, during purification, the astaxanthin-containing shrimp protein deposit is placed in a digestion tank, and vegetable oil is added, followed by stirring, heating to 58° C., adding of purified water at a mass ratio of 1:1, and emulsification; wherein the temperature difference between the mixture of shrimp protein deposit and vegetable oil and the added water is not more than 1° C. Saponification will be caused if the temperature difference is too high or too low, and the astaxanthin dissolved in the oil after the saponification cannot be separated.

Further, the vegetable oil may be one or more of soybean oil, safflower seed oil, corn oil, and tea oil.

Further, in S6, during the centrifuging, the centrifuging rate is 5500-6500 r/min, and the centrifuging time is 10-14 min.

Further, the shrimp protein obtained in S6 may be washed with pure water, centrifuged, and spray-dried to obtain dry shrimp protein powder.

Optionally, the astaxanthin-containing oil is further defatted and dried to obtain astaxanthin. Further, the method further includes steps of extracting useful substances from the solid residues obtained in S3, including:

S3.1, decolorizing the solid residues, then mixing the decolorized solid residues with water at a mass ratio of 1:(1.2-1.8), then adjusting the pH value to 2.5-3.5 with citric acid, controlling the temperature to 50-60° C., stirring for 8-10 h at a speed of 45-55 r/min, and performing solid-liquid separation to obtain calcium-containing liquid and decalcified solid residues;

S3.2, concentrating the calcium-containing liquid obtained in S3.1 and performing spray drying to obtain calcium citrate powder;

mixing the decalcified solid residues obtained in S3.1 with water at a mass ratio of (1-2):(1-2), adding NaOH, adjusting the pH value to 13-14, then heating to 42-48° C., stirring at a constant temperature for 10-12 h, and performing solid-liquid separation to obtain solid substances, wherein acetyl substances can be removed from the decalcified solid residues in this step; and S3.3, milling the solid substances obtained in S3.2 into a colloidal solution with a colloid mill, then mixing the colloidal solution with water at a mass ratio of 1:(1.5-2.5), adjusting the pH value to 3.0-3.2, heating to 45-55° C., stirring at a constant temperature for 6-10 h, performing solid-liquid separation, concentrating and spray-drying the liquid components obtained by the solid-liquid separation to obtain water-soluble chitosan, and drying and milling the solid components obtained by the solid-liquid separation to obtain water-insoluble chitosan.

The method is simple in operation, environmentally friendly, pollution-free, and low in equipment requirements, the raw materials are sufficient and can be fully utilized, and therefore, four substances can be extracted at the same time, with short production cycle and high product quality. Further, in S3.1, during the decolorizing process, the solid residues and water are mixed at a mass ratio of 1:(1.2-1.8), heated to 42-48° C., then added with hydrogen peroxide, and stirred for 2-4 h, and solid-liquid separation is performed to obtain decolorized solid residues.

The inventor found, when water is added in S5, the temperature difference between the mixture of vegetable oil and shrimp protein deposit and the water cannot be more than 1° C., and if the temperature difference is too high, the chaotically solidified solution, oil, astaxanthin, and protein cannot be separated. Vegetable oil does not dissolve when added to water, and tiny droplets are evenly dispersed in immiscible water after shaking, showing a liquid-liquid interface. The astaxanthin contained in the protein, which is soluble in oil but insoluble in water, can be separated from the shrimp protein. The oil and water are delaminated due to different densities, the oil with low density is in the upper layer, the water with high density is in the lower layer of oil, and the shrimp protein is deposited in the bottom layer.

The method of the present invention uses waste biomass obtained after shrimps processed as a raw material, and can simultaneously extract four high-value substances, thereby not only improving the utilization rate of raw materials, but also shortening the production cycle; and no organic solvent is added, such that the method is clean, green and environmentally friendly.

Compared with the prior art, the beneficial effects of the present invention are as follows:

1. The method of the present invention has simple extraction steps, low cost required, and high extraction rate.

2. When astaxanthin is extracted using the method of the present invention, the extraction rate is 85% or more, with good quality and high stability.

3. The method of the present invention is environmentally friendly and free of acid, alkali and organic solvent pollution, and can be used for large-scale continuous production.

4. The method of the present invention provides a new way to treat shrimp processing scraps, and also provides abundant raw materials for the extraction of astaxanthin and shrimp protein. The method of the present invention uses waste substances as raw materials, and can extract multiple substances at the same time.

DETAILED DESCRIPTION OF THE EMBODIMENTS

Example 1: A method for extracting astaxanthin and shrimp protein from crayfish shells by a biological enzyme method included the following steps:
Step 1, crayfish shells (including heads and tails) were pretreated, and 100 kg of frozen crayfish shells were minced into 20-50 mm fragments with a meat mincer.
Step 2, the crayfish shell fragments and water at a ratio of 1:1 were put into a reaction tank and heated to 30-40° C. with a pH value of 7.0, and the biological alkaline enzyme powder (manufacturer: Nanning Pangbo Biological Engineering Co., Ltd., specification 200u) was added into the mixture of the crayfish shell fragments and water at a mass ratio of 1:1000, followed by stirring at a constant temperature of 45° C. and a speed of 45-60 r/min, and digestion for 60 min, thus obtaining 100 kg of enzymatic hydrolysate.
Step 3, the 100 kg of enzymatic hydrolysate obtained was centrifuged to obtain 17.4 kg of astaxanthin-rich shrimp protein pulp.
Step 4, the 17.4 kg of astaxanthin-rich shrimp protein pulp was placed in a digestion tank, 7 kg of vegetable oil was added, the pulp was heated to 58° C., 58.5° C. pure water was added at a mass ratio of 6:4, stirring was performed for 60 min, then centrifugation was performed to obtain 12.6 kg of solid shrimp protein in the lower layer and 550 g of astaxanthin oil containing 6.1 wt % astaxanthin in the upper layer, and defatting and drying were performed to obtain 33550 mg of 99 wt % high-purity astaxanthin.

Optionally, after the enzymolysis, the solid residues obtained were placed in a digestion tank for decolorization, hydrogen peroxide was added at a ratio of 1000 g:13 ml, followed by stirring for 3 h. After the decolorization was completed, the solution was placed in the digestion tank for decalcification. The pH value was adjusted to 3.0-3.2 with citric acid, followed by stirring at a constant temperature to 50° C., digestion for 10 h, and solid-liquid separation, thus obtaining calcium-containing liquid and decalcified solid residues.

Solid filtration: centrifugal drying was performed on the calcium-containing liquid to obtain calcium citrate, the decalcified solid residues were placed in the digestion tank for deacetylation, the pH value was adjusted to 13.5 with NaOH, the decalcified solid residues were digested for 12 h, solids were filtered (the filtrate was recycled), the deacetylated solids weremilled by a colloid mill, the obtained colloidal solution was placed in the digestion tank for dissolution, the pH value was adjusted to 3.0 with glacial acetic acid, the solids weredissolved for 8 h, finally the pH value was adjusted to 6.8 with NaOH, filtration was performed again, the obtained liquid was concentrated, the concentrate was dried to obtain 27000 mg of water-soluble chitosan, and the obtained solids were dried and milled to obtain 34000 mg of water-insoluble chitosan.

Example 2: A method for extracting astaxanthin and shrimp protein from sea shrimp shells by a biological enzyme method included the following steps:
Step 1, frozen sea shrimp shells (including heads and tails) were minced into 20-50 mm fragments.
Step 2, the minced shrimp shell fragments and water at a ratio of 1:1 were put into a reaction tank and heated to 30° C. to 40° C., with a pH value of 6.8-7.0. The biological alkaline enzyme powder was added into the mixture of the minced shrimp shell fragments and water at a mass ratio of 1:1000, followed by stirring at a constant temperature of 45° C. and a speed of 50 r/min, and digestion for 90 min, thus obtaining 100 kg of enzymatic hydrolysate.
Step 3, the 100 kg of enzymatic hydrolysate obtained was centrifuged to obtain 16.5 kg of astaxanthin-rich shrimp protein pulp.
Step 4, the 16.5 kg of astaxanthin-rich shrimp protein pulp was placed in a digestion tank, 7 kg of vegetable oil was added, the pulp was stirred and heated to 55° C., 56° C. pure water was added at a mass ratio of 6:4, stirring was performed at a constant temperature for 60 min, and centrifugation was performed to obtain 9.7 kg of solid shrimp protein in the lower layer and 420 g of dark red astaxanthin oil liquid, and defatting and drying were performed to obtain 25620 mg of 99 wt % astaxanthin.

Optionally, after the enzymolysis, the solid residues obtained were placed in a digestion tank for decolorization, hydrogen peroxide was added at a ratio of 1000 g:13 mL, followed by stirring for 3 h. After the decolorization was completed, the solution was placed in the digestion tank for decalcification. The pH value was adjusted to 3.0-3.2 with citric acid, followed by stirring at a constant temperature to 50° C., digestion for 10 h, and solid-liquid separation, thus obtaining calcium-containing liquid and decalcified solid residues.

Solid filtration: centrifugal drying was performed on the calcium-containing liquid to obtain calcium citrate, the decalcified solid residues were placed in the digestion tank for deacetylation, the pH value was adjusted to 13.5 with NaOH, the decalcified solid residues were digested for 12 h, solids were filtered (the filtrate was recycled), the deacetylated solids were milled by a colloid mill, the obtained colloidal solution was placed in the digestion tank for dissolution, the pH value was adjusted to 3.0 with glacial acetic acid, the solids were dissolved for 8 h, finally the pH value was adjusted to 6.8 with NaOH, filtration was performed again, the obtained liquid was concentrated, the concentrate was dried to obtain 20150 mg of water-soluble chitosan, and the obtained solids were dried and milled to obtain 18460 mg of water-insoluble chitosan.

The applicant repeated Examples 1 and 2 and only changed the temperature when pure water was added in step 4. When the difference between the initial temperature of the pure water and the temperature of the mixture of shrimp protein pulp and oil was more than 1° C., saponification will occur. As a result, it was difficult to separate astaxanthin.

Specifically, in order to further confirm the importance of controlling the temperature difference within 1° C. in step 4, a further relevant case was provided as follows: Example 1 was repeated, except that: in step 4, pure water at T° C. was added (the mass ratio of water to shrimp protein deposit was 6:4), and emulsification was performed for 60 min under stirring to obtain an emulsion; then the emulsion was centrifuged and delaminated to obtain astaxanthin oil in the upper layer, water in the middle layer and shrimp protein in the bottom layer. The above experiment was repeated using the same batch of astaxanthin-containing shrimp protein deposit as a raw material and the temperature T of the added water as a variable. The situations of the astaxanthin-containing oil that can be finally separated were shown in Table 1.

TABLE 1

Situations of astaxanthin-containing oil that can be separated by adding T° C. pure water Constant temperature 58° C. in digestion tank

| T/° C. | 48 | 49 | 50 | 51 | 52 | 53 | 54 |
|---|---|---|---|---|---|---|---|
| Mass of astaxanthin oil/g | 88 | 120 | 200 | 245 | 271 | 355 | 385 |
| T/° C. | 55 | 56 | 57 | 58 | 59 | 60 | 61 |
| Mass of astaxanthin oil/g | 445 | 480 | 520 | 554 | 540 | 520 | 460 |
| T/° C. | 62 | 63 | 64 | 65 | 66 | 67 | 68 |
| Mass of astaxanthin oil/g | 445 | 395 | 350 | 320 | 265 | 187 | 130 |

The above tests proved that during the purification and emulsification, the temperature difference between the oil phase and the added water had a great impact on the separation of astaxanthin; when water was added to the oil phase, the greater the temperature difference between oil and water was, the lower the quality of the astaxanthin-containing oil obtained was, and the worse the purification effect was; only when the temperature difference between oil and water was within 1° C., the emulsification, separation and purification effects were the best. The main reason was that the emulsification was incomplete and even serious saponification occurred due to the influence of temperature, which affected the separation of the astaxanthin-containing oil and resulted in poor separation of astaxanthin. It can be seen that this application can avoid the saponification phenomenon and achieve a good separation effect by controlling the temperature difference between oil and water within 1° C.

It can be seen that the practices of separating astaxanthin and shrimp protein from the shrimp protein deposit by using vegetable oil and water and controlling the temperature difference between oil and water can effectively solve the problem of deep extraction of shrimp protein and astaxanthin from the enzymatic hydrolysate, and have obvious advantages compared with the existing technologies such as oil extraction.

The above examples are only to illustrate the technical concept and technical features of the present invention, and cannot be used to limit the protection scope of the present invention. Any equivalent modification based on the essence of the present invention should fall within the protection scope of the present invention.

The invention claimed is:

1. A method for extracting substances from shrimp shells, comprising the following steps:
S1, crushing the shrimp shells to obtain fragments;
S2, mixing the fragments obtained in S1 with water at a mass ratio of 1-2:1-2 to obtain a mixture;
S3, heating the mixture obtained in S2 to 28-35° C., then adjusting the pH value to 6.8-7.5, adding an alkaline protease, mixing, heating to 42-48° C., performing constant-temperature enzymolysis, and sieving to obtain enzymatic hydrolysate and solid residues, wherein the mass ratio of the alkaline protease to the mixture is 1:800-1200, and continuous stirring at a rate of 45-60 r/min is required during the enzymolysis;
S4, performing centrifugal separation on the enzymatic hydrolysate obtained in S3 to obtain an astaxanthin-containing shrimp protein deposit;
S5, mixing the astaxanthin-containing shrimp protein deposit obtained in S4 with vegetable oil, heating to 57-60° C. while stirring, adding water, and emulsifying for 50-70 min under stirring to obtain an emulsion, wherein the mass ratio of the water to the shrimp protein deposit is 1.2-1.8:1, and the temperature difference between the mixture of shrimp protein deposit and vegetable oil and the added water is not more than 1° C.; and
S6, centrifuging the emulsion in S5, and delaminating to obtain astaxanthin-containing oil in an upper layer, water in a middle layer, and a shrimp protein in a lower layer;
wherein the shrimp is selected from the group of freshwater shrimp and sea shrimp.

2. The method according to claim 1, wherein in S1, the fragments have a size of 4-9 cm$^2$.

3. The method according to claim 1, wherein in S3, the sieving is performed through an 80-mesh vibrating screen.

4. The method according to claim 1, wherein in S3, the constant-temperature enzymolysis time is 50-90 min.

5. The method according to claim 4, wherein in S3, the constant-temperature enzymolysis time is 50-70 min.

6. The method according to claim 1, wherein in S4, during the centrifugal separation, the centrifugal rate is 4000-5000 r/min, and the centrifugal time is 10-14 min.

7. The method according to claim 1 wherein in S5, the pH value is adjusted with glacial acetic acid or hydrochloric acid.

8. The method according to claim 1, wherein in S5, the temperature difference between the mixture of shrimp protein deposit and vegetable oil and the added water is not more than 0.5° C.

9. The method according to claim 1, wherein in S6, during the centrifuging, the centrifuging rate is 5500-6500 r/min, and the centrifuging time is 10-14 min.

10. The method according to claim 1, further comprising steps of extracting substances from the solid residues obtained in S3, comprising:
S3A, decolorizing the solid residues, then mixing the decolorized solid residues with water at a mass ratio of 1:1.2-1.8, then adjusting the pH value to 2.5-3.5 with citric acid, controlling the temperature to 50-60° C., stirring for 8-10 h at a speed of 45-55 r/min, and performing solid-liquid separation to obtain calcium-containing liquid and decalcified solid residues;
S3B, concentrating the calcium-containing liquid obtained in S3a and performing spray drying to obtain calcium citrate powder; mixing the decalcified solid residues obtained in S3A with water at a mass ratio of 1-2:1-2, adding NaOH, adjusting the pH value to 13-14, then heating to 42-48° C., stirring at a constant temperature for 10-12 h, and performing solid-liquid separation to obtain solid substances; and
S3C, milling the solid substances obtained in S3B into a colloidal solution with a colloid mill, then mixing the colloidal solution with water at a mass ratio of 1:1.5-2.5, adjusting the pH value to 3.0-3.2, heating to 45-55° C., stirring at a constant temperature for 6-10 h, performing solid-liquid separation, concentrating and spray-drying the liquid components obtained by the solid-liquid separation to obtain water-soluble chitosan, and drying and milling the solid components obtained by the solid-liquid separation to obtain water-insoluble chitosan.

11. The method according to claim 2, further comprising steps of extracting substances from the solid residues obtained in S3, comprising:
S3A, decolorizing the solid residues, then mixing the decolorized solid residues with water at a mass ratio of 1:1.2-1.8, then adjusting the pH value to 2.5-3.5 with citric acid, controlling the temperature to 50-60° C., stirring for 8-10 h at a speed of 45-55 r/min, and performing solid-liquid separation to obtain calcium-containing liquid and decalcified solid residues;
S3B, concentrating the calcium-containing liquid obtained in S3A and performing spray drying to obtain calcium citrate powder;
mixing the decalcified solid residues obtained in S3A with water at a mass ratio of 1-2:1-2, adding NaOH, adjusting the pH value to 13-14, then heating to 42-48° C., stirring at a constant temperature for 10-12 h, and performing solid-liquid separation to obtain solid substances; and
S3C, milling the solid substances obtained in S3B into a colloidal solution with a colloid mill, then mixing the colloidal solution with water at a mass ratio of 1:1.5-2.5, adjusting the pH value to 3.0-3.2, heating to 45-55° C., stirring at a constant temperature for 6-10 h, performing solid-liquid separation, concentrating and spray-drying the liquid components obtained by the solid-liquid separation to obtain water-soluble chitosan, and drying and milling the solid components obtained by the solid-liquid separation to obtain water-insoluble chitosan.

12. The method according to claim 3, further comprising steps of extracting substances from the solid residues obtained in S3, comprising:
S3A, decolorizing the solid residues, then mixing the decolorized solid residues with water at a mass ratio of 1:1.2-1.8, then adjusting the pH value to 2.5-3.5 with citric acid, controlling the temperature to 50-60° C., stirring for 8-10 h at a speed of 45-55 r/min, and performing solid-liquid separation to obtain calcium-containing liquid and decalcified solid residues;
S3B, concentrating the calcium-containing liquid obtained in S3A and performing spray drying to obtain calcium citrate powder; mixing the decalcified solid residues obtained in S3A with water at a mass ratio of 1-2:1-2, adding NaOH, adjusting the pH value to 13-14, then heating to 42-48° C., stirring at a constant temperature for 10-12 h, and performing solid-liquid separation to obtain solid substances; and
S3C, milling the solid substances obtained in S3B into a colloidal solution with a colloid mill, then mixing the colloidal solution with water at a mass ratio of 1:1.5-2.5, adjusting the pH value to 3.0-3.2, heating to 45-55° C. stirring at a constant temperature for 6-10 h, performing solid-liquid separation, concentrating and spray-drying the liquid components obtained by the solid-liquid separation to obtain water-soluble chitosan, and drying and milling the solid components obtained by the solid-liquid separation to obtain water-insoluble chitosan.

13. The method according to claim 4, further comprising steps of extracting substances from the solid residues obtained in S3, comprising:
S3A, decolorizing the solid residues, then mixing the decolorized solid residues with water at a mass ratio of 1:1.2-1.8, then adjusting the pH value to 2.5-3.5 with citric acid, controlling the temperature to 50-60° C., stirring for 8-10 h at a speed of 45-55 r/min, and performing solid-liquid separation to obtain calcium-containing liquid and decalcified solid residues;
S3B, concentrating the calcium-containing liquid obtained in S3A and performing spray drying to obtain calcium citrate powder; mixing the decalcified solid residues obtained in S3A with water at a mass ratio of 1-2:1-2, adding NaOH, adjusting the pH value to 13-14, then heating to 42-48° C., stirring at a constant temperature for 10-12 h, and performing solid-liquid separation to obtain solid substances; and
S3C, milling the solid substances obtained in S3B into a colloidal solution with a colloid mill, then mixing the colloidal solution with water at a mass ratio of 1:1.5-2.5, adjusting the pH value to 3.0-3.2, heating to 45-55° C., stirring at a constant temperature for 6-10 h, performing solid-liquid separation, concentrating and spray-drying the liquid components obtained by the solid-liquid separation to obtain water-soluble chitosan, and drying and milling the solid components obtained by the solid-liquid separation to obtain water-insoluble chitosan.

14. The method according to claim 5, further comprising steps of extracting substances from the solid residues obtained in S3, comprising:
S3A, decolorizing the solid residues, then mixing the decolorized solid residues with water at a mass ratio of 1:1.2-1.8, then adjusting the pH value to 2.5-3.5 with citric acid, controlling the temperature to 50-60° C., stirring for 8-10 h at a speed of 45-55 r/min, and performing solid-liquid separation to obtain calcium-containing liquid and decalcified solid residues;
S3B, concentrating the calcium-containing liquid obtained in S3A and performing spray drying to obtain calcium citrate powder; mixing the decalcified solid residues obtained in S3A with water at a mass ratio of 1-2:1-2, adding NaOH, adjusting the pH value to 13-14, then heating to 42-48° C., stirring at a constant temperature for 10-12 h, and performing solid-liquid separation to obtain solid substances; and
S3C, milling the solid substances obtained in S3B into a colloidal solution with a colloid mill, then mixing the colloidal solution with water at a mass ratio of 1:1.5-2.5, adjusting the pH value to 3.0-3.2, heating to 45-55° C., stirring at a constant temperature for 6-10 h, performing solid-liquid separation, concentrating and spray-drying the liquid components obtained by the solid-liquid separation to obtain water-soluble chitosan, and drying and milling the solid components obtained by the solid-liquid separation to obtain water-insoluble chitosan.

15. The method according to claim 6, further comprising steps of extracting substances from the solid residues obtained in S3, comprising:
S3A, decolorizing the solid residues, then mixing the decolorized solid residues with water at a mass ratio of 1:1.2-1.8, then adjusting the pH value to 2.5-3.5 with citric acid, controlling the temperature to 50-60° C., stirring for 8-10 h at a speed of 45-55 r/min, and performing solid-liquid separation to obtain calcium-containing liquid and decalcified solid residues;
S3B, concentrating the calcium-containing liquid obtained in S3A and performing spray drying to obtain calcium citrate powder; mixing the decalcified solid residues obtained in S3A with water at a mass ratio of 1-2:1-2, adding NaOH, adjusting the pH value to 13-14, then heating to 42-48° C., stirring at a constant temperature for 10-12 h, and performing solid-liquid separation to obtain solid substances; and S3C, milling the solid substances obtained in S3B into a colloidal solution with a colloid mill, then mixing the colloidal solution with water at a mass ratio of 1:1.5-2.5, adjusting the pH value to 3.0-3.2, heating to 45-55° C., stirring at a constant temperature for 6-10 h, performing solid-liquid separation, concentrating and spray-drying the liquid components obtained by the solid-liquid separation to obtain water-soluble chitosan, and drying and milling the solid components obtained by the solid-liquid separation to obtain water-insoluble chitosan.

16. The method according to claim 7, further comprising steps of extracting substances from the solid residues obtained in S3, comprising:

S3A, decolorizing the solid residues, then mixing the decolorized solid residues with water at a mass ratio of 1:1.2-1.8, then adjusting the pH value to 2.5-3.5 with citric acid, controlling the temperature to 50-60° C., stirring for 8-10 h at a speed of 45-55 r/min, and performing solid-liquid separation to obtain calcium-containing liquid and decalcified solid residues;

S3B, concentrating the calcium-containing liquid obtained in S3A and performing spray drying to obtain calcium citrate powder; mixing the decalcified solid residues obtained in S3A with water at a mass ratio of 1-2:1-2, adding NaOH, adjusting the pH value to 13-14, then heating to 42-48° C., stirring at a constant temperature for 10-12 h, and performing solid-liquid separation to obtain solid substances; and S3C, milling the solid substances obtained in S3B into a colloidal solution with a colloid mill, then mixing the colloidal solution with water at a mass ratio of 1:1.5-2.5, adjusting the pH value to 3.0-3.2, heating to 45-55° C., stirring at a constant temperature for 6-10 h, performing solid-liquid separation, concentrating and spray-drying the liquid components obtained by the solid-liquid separation to obtain water-soluble chitosan, and drying and milling the solid components obtained by the solid-liquid separation to obtain water-insoluble chitosan.

17. The method according to claim 8, further comprising steps of extracting substances from the solid residues obtained in S3, comprising:

S3A, decolorizing the solid residues, then mixing the decolorized solid residues with water at a mass ratio of 1:1.2-1.8, then adjusting the pH value to 2.5-3.5 with citric acid, controlling the temperature to 50-60° C., stirring for 8-10 h at a speed of 45-55 r/min, and performing solid-liquid separation to obtain calcium-containing liquid and decalcified solid residues;

S3B, concentrating the calcium-containing liquid obtained in S3A and performing spray drying to obtain calcium citrate powder; mixing the decalcified solid residues obtained in S3A with water at a mass ratio of 1-2:1-2, adding NaOH, adjusting the pH value to 13-14, then heating to 42-48° C., stirring at a constant temperature for 10-12 h, and performing solid-liquid separation to obtain solid substances; and S3C, milling the solid substances obtained in S3B into a colloidal solution with a colloid mill, then mixing the colloidal solution with water at a mass ratio of 1:1.5-2.5, adjusting the pH value to 3.0-3.2, heating to 45-55° C., stirring at a constant temperature for 6-10 h, performing solid-liquid separation, concentrating and spray-drying the liquid components obtained by the solid-liquid separation to obtain water-soluble chitosan, and drying and milling the solid components obtained by the solid-liquid separation to obtain water-insoluble chitosan.

18. The method according to claim 9, further comprising steps of extracting substances from the solid residues obtained in S3, comprising:

S3A, decolorizing the solid residues, then mixing the decolorized solid residues with water at a mass ratio of 1:1.2-1.8, then adjusting the pH value to 2.5-3.5 with citric acid, controlling the temperature to 50-60° C., stirring for 8-10 h at a speed of 45-55 r/min, and performing solid-liquid separation to obtain calcium-containing liquid and decalcified solid residues;

S3B, concentrating the calcium-containing liquid obtained in S3A and performing spray drying to obtain calcium citrate powder; mixing the decalcified solid residues obtained in S3A with water at a mass ratio of 1-2:1-2, adding NaOH, adjusting the pH value to 13-14, then heating to 42-48° C., stirring at a constant temperature for 10-12 h, and performing solid-liquid separation to obtain solid substances; and S3C, milling the solid substances obtained in S3B into a colloidal solution with a colloid mill, then mixing the colloidal solution with water at a mass ratio of 1:1.5-2.5, adjusting the pH value to 3.0-3.2, heating to 45-55° C., stirring at a constant temperature for 6-10 h, performing solid-liquid separation, concentrating and spray-drying the liquid components obtained by the solid-liquid separation to obtain water-soluble chitosan, and drying and milling the solid components obtained by the solid-liquid separation to obtain water-insoluble chitosan.

19. The method according to claim 10, wherein in S3A, during the decolorizing, the solid residues and water are mixed at a mass ratio of 1:1.2-1.8, heated to 42-48° C., then added with hydrogen peroxide, and stirred for 2-4 h, and solid-liquid separation is performed to obtain decolorized solid residues.

* * * * *